United States Patent
Fung et al.

(10) Patent No.: US 10,213,162 B2
(45) Date of Patent: Feb. 26, 2019

(54) SYSTEM AND METHOD FOR CAPTURING AND DECONTAMINATING PHOTOPLETHYSMOPGRAPHY (PPG) SIGNALS IN A VEHICLE

(71) Applicant: Honda Motor Co., Ltd., Tokyo (JP)

(72) Inventors: Kin C. Fung, Dublin, OH (US);
Timothy J. Dick, Dublin, OH (US);
Dhanashree Palande, Dublin, OH (US)

(73) Assignee: Honda Motor Co., Ltd., Tokyo (JP)

( * ) Notice: Subject to any disclaimer, the term of this patent is extended or adjusted under 35 U.S.C. 154(b) by 120 days.

(21) Appl. No.: 15/235,808

(22) Filed: Aug. 12, 2016

(65) Prior Publication Data
US 2016/0345907 A1   Dec. 1, 2016

Related U.S. Application Data

(63) Continuation-in-part of application No. 14/697,593, filed on Apr. 27, 2015, which is a continuation-in-part
(Continued)

(51) Int. Cl.
*A61B 5/18* (2006.01)
*A61B 5/00* (2006.01)
(Continued)

(52) U.S. Cl.
CPC .......... *A61B 5/6893* (2013.01); *A61B 5/0261* (2013.01); *A61B 5/0295* (2013.01);
(Continued)

(58) Field of Classification Search
CPC . A61B 5/14532; A61B 5/0295; A61B 5/6893; A61B 5/721; G06K 9/0053; B60R 25/25
See application file for complete search history.

(56) References Cited

U.S. PATENT DOCUMENTS 4,653,498 A   3/1987   New, Jr. et al.
5,173,661 A   12/1992  Knüttel et al.
(Continued)

FOREIGN PATENT DOCUMENTS

DE   102005020847   11/2006
DE   102008042342   4/2010
(Continued)

OTHER PUBLICATIONS

Office Action of U.S. Appl. No. 14/961,277 dated Feb. 12, 2018, 73 pages.
(Continued)

*Primary Examiner* — Roy Y Yi
*Assistant Examiner* — Jeffrey Aiello
(74) *Attorney, Agent, or Firm* — Rankin, Hill & Clark LLP

(57) ABSTRACT

A system and method for processing photoplethysmography (PPG) signals in a vehicle. The system and method include receiving a PPG waveform signal from an optical sensor. The system and method also include processing a PPG measurement signal based on the PPG waveform signal. The system and method additionally include receiving a noise waveform signal from at least one of: a seat assembly sensor, a vehicle sensor, and a vehicle system. Additionally, the system and method include processing a motion artifacts measurement signal based on the noise waveform signal. The system and method further include processing a refined PPG signal to suppress the motion artifacts measurement signal from the PPG measurement signal.

20 Claims, 5 Drawing Sheets

Related U.S. Application Data of application No. 13/858,038, filed on Apr. 6, 2013, now Pat. No. 9,272,689.

(51) Int. Cl.

| | | |
|---|---|---|
| *A61B 5/11* | (2006.01) | |
| *A61B 5/1455* | (2006.01) | |
| *A61B 5/026* | (2006.01) | |
| *B60R 25/25* | (2013.01) | |
| *G06K 9/00* | (2006.01) | |
| *A61B 5/0295* | (2006.01) | |
| *A61B 5/08* | (2006.01) | |
| *A61B 5/024* | (2006.01) | |
| *A61B 5/117* | (2016.01) | |

(52) U.S. Cl.
CPC ............ *A61B 5/11* (2013.01); *A61B 5/14552* (2013.01); *A61B 5/18* (2013.01); *A61B 5/721* (2013.01); *B60R 25/25* (2013.01); *G06K 9/0053* (2013.01); *G06K 9/00536* (2013.01); *A61B 5/0059* (2013.01); *A61B 5/0077* (2013.01); *A61B 5/02416* (2013.01); *A61B 5/0816* (2013.01); *A61B 5/117* (2013.01); *G06K 2009/00939* (2013.01)

(56) References Cited

U.S. PATENT DOCUMENTS

| | | | |
|---|---|---|---|
| 5,369,601 A * | 11/1994 | Tannenbaum | A63B 69/00 |
| | | | 702/139 |
| 5,521,823 A * | 5/1996 | Akita | B60G 17/0195 |
| | | | 180/170 |
| 5,617,871 A | 4/1997 | Burrows | |
| 5,719,950 A | 2/1998 | Osten et al. | |
| 6,026,340 A * | 2/2000 | Corrado | B60N 2/002 |
| | | | 280/735 |
| 6,198,996 B1 | 3/2001 | Berstis | |
| 6,271,745 B1 | 8/2001 | Anzai et al. | |
| 6,810,309 B2 | 10/2004 | Sadler et al. | |
| 6,993,378 B2 | 1/2006 | Wiederhold et al. | |
| 7,147,601 B2 | 12/2006 | Marks et al. | |
| 7,149,653 B2 | 12/2006 | Bihler et al. | |
| 7,330,570 B2 | 2/2008 | Sogo et al. | |
| 7,403,804 B2 | 7/2008 | Ridder et al. | |
| 7,689,271 B1 | 3/2010 | Sullivan | |
| 7,756,558 B2 | 7/2010 | Ridder et al. | |
| 7,800,592 B2 | 9/2010 | Kerr et al. | |
| 7,933,315 B2 | 4/2011 | Li et al. | |
| 7,946,483 B2 | 5/2011 | Millet et al. | |
| 7,948,361 B2 | 5/2011 | Bennett et al. | |
| 8,068,562 B1 | 11/2011 | Zhang et al. | |
| 8,706,204 B2 | 4/2014 | Seo et al. | |
| 8,764,676 B2 | 7/2014 | Prakash et al. | |
| 8,773,239 B2 | 7/2014 | Phillips et al. | |
| 8,886,294 B2 | 11/2014 | Lisogurski et al. | |
| 8,930,145 B2 | 1/2015 | Li et al. | |
| 9,149,231 B2 | 10/2015 | Fujita et al. | |
| 9,751,534 B2 | 9/2017 | Fung et al. | |
| 2002/0097145 A1 | 7/2002 | Tumey et al. | |
| 2002/0156364 A1 | 10/2002 | Madore | |
| 2002/0176511 A1 | 11/2002 | Fullerton et al. | |
| 2004/0088095 A1 | 5/2004 | Eberle et al. | |
| 2005/0058456 A1 | 3/2005 | Yoo | |
| 2005/0155808 A1 | 7/2005 | Braeuchle et al. | |
| 2005/0156457 A1 * | 7/2005 | Breed | B60N 2/002 |
| | | | 297/467 |
| 2005/0242808 A1 | 11/2005 | McKendry et al. | |
| 2006/0180764 A1 * | 8/2006 | Yajima | B60R 21/01534 |
| | | | 250/349 |
| 2006/0208169 A1 * | 9/2006 | Breed | B60N 2/002 |
| | | | 250/221 |
| 2007/0159344 A1 | 7/2007 | Kisacanin | |
| 2007/0237218 A1 | 10/2007 | Walker | |
| 2008/0027337 A1 | 1/2008 | Dugan et al. | |
| 2008/0146892 A1 | 6/2008 | LeBoeuf et al. | |
| 2008/0312376 A1 | 12/2008 | Mas et al. | |
| 2009/0027261 A1 | 1/2009 | Martin et al. | |
| 2009/0046538 A1 | 2/2009 | Breed et al. | |
| 2009/0054751 A1 | 2/2009 | Babashan et al. | |
| 2009/0284361 A1 | 11/2009 | Boddie et al. | |
| 2010/0066137 A1 | 3/2010 | Sakai et al. | |
| 2010/0113950 A1 | 5/2010 | Lin et al. | |
| 2010/0155609 A1 | 6/2010 | Silva | |
| 2010/0160794 A1 | 6/2010 | Banet et al. | |
| 2010/0217102 A1 | 8/2010 | LeBoeuf et al. | |
| 2011/0009754 A1 * | 1/2011 | Wenzel | A61B 5/0215 |
| | | | 600/485 |
| 2011/0066007 A1 | 3/2011 | Banet et al. | |
| 2011/0066042 A1 | 3/2011 | Pandia et al. | |
| 2011/0314737 A1 * | 12/2011 | Schindhelm | E05F 15/70 |
| | | | 49/31 |
| 2012/0290215 A1 | 11/2012 | Adler et al. | |
| 2013/0060480 A1 | 3/2013 | Korhonen et al. | |
| 2013/0172771 A1 | 7/2013 | Muhlsteff | |
| 2013/0179163 A1 | 7/2013 | Herbig et al. | |
| 2013/0183646 A1 | 7/2013 | Lusted et al. | |
| 2013/0204466 A1 * | 8/2013 | Ricci | G06F 17/00 |
| | | | 701/2 |
| 2013/0245886 A1 | 9/2013 | Fung et al. | |
| 2013/0261415 A1 * | 10/2013 | Ashe | A61B 5/14552 |
| | | | 600/324 |
| 2013/0296666 A1 | 11/2013 | Kumar et al. | |
| 2014/0039330 A1 * | 2/2014 | Seo | A61B 5/0452 |
| | | | 600/509 |
| 2014/0058217 A1 | 2/2014 | Giovangrandi | |
| 2014/0073963 A1 | 3/2014 | Engelbrecht et al. | |
| 2014/0121927 A1 | 5/2014 | Hanita | |
| 2014/0188770 A1 | 7/2014 | Agrafioti et al. | |
| 2014/0228649 A1 | 8/2014 | Rayner et al. | |
| 2014/0275854 A1 | 9/2014 | Venkatraman et al. | |
| 2014/0275886 A1 | 9/2014 | Teixeira | |
| 2014/0303899 A1 | 10/2014 | Fung et al. | |
| 2015/0148691 A1 | 5/2015 | Moyer et al. | |

FOREIGN PATENT DOCUMENTS

| | | |
|---|---|---|
| DE | 102012208644 | 5/2013 |
| DE | 102012020901 | 4/2014 |
| DE | 102013200777 | 7/2014 |
| DE | 102013010928 | 12/2014 |
| EP | 2591969 | 5/2013 |
| JP | 2012212362 | 11/2012 |
| JP | 2012533474 | 12/2012 |
| WO | 2011038803 | 4/2011 |
| WO | 2012115220 | 8/2012 |
| WO | 2013164724 | 11/2013 |
| WO | 2014128273 | 8/2014 |

OTHER PUBLICATIONS

Search Report of DE Serial No. 10 2014 206 648.4 dated Nov. 26, 2014, 9 pages.

Search Report of DE Serial 10 2014 206 648.4 dated Nov. 26, 2014, 8 pages. (English translation).

Internet Video: CEATEC new chip detects motion, heartbeats—Videos (news)—PC Advisor printed Jan. 17, 2012.

Kavsaoğlu et al.: "A novel feature ranking algorithm for biometric recognition with PPG signals", Computers in Biology and Medicine vol. 49, 2014, pp. 1-14.

Murata et al.: "Noninvasive Biological Sensor System for Detection of Drunk Driving", IEEE Transactions on Information Technology in Biomedicine, vol. 15, No. 1, Jan. 2011.

TruTouch Technologies: "Technology Overview" pp. 1-4, printed Apr. 27, 2015.

Brown et al.: "Framework for Multivariate Selectivity Analysis, Part I: Theoretical and Practical Merits", Applied Spectroscopy, vol. 59, No. 6, 2005, pp. 787-803.

Ridder et al.: "Framework for Multivariate Selectivity Analysis, Part II: Experimental Applications", Applied Spectroscopy, vol. 59, No. 6, 2005, pp. 804-815.

(56) References Cited

OTHER PUBLICATIONS

Press Release: "Faurecia keeps travelers fit, healthier in a heartbeat with "Active Wellness" car seat", Apr. 20, 2015.
Press Release: "Hoana Partners with Automotive Seat Manufacturer Faurecia to Introduce "Active Wellness™" at Auto Shanghai 2015", Apr. 20, 2015.
YouTube Video Link: https://www.youtube.com/watch?feature=youtu.be&v=_1UBDFSzQ28&app=desktop, printed on Apr. 27, 2015.
Article: http://www.faurecia.cn/jian-kang-mai-bo-fo-ji-ya-active-wellness-zuo-yi-wei-jia-cheng-zhe-jian-kang-hu-hang, printed on Apr. 27, 2015.
TruTouch Technologies prototype, Driver Alcohol Detection System for Safety, www.DADSS.org, 1 page.
Office Action of U.S. Appl. No. 13/858,038 dated Jun. 26, 2015, 19 pages.
International Search Report and Written Opinion of PCT/US2015/037019 dated Nov. 2, 2015, 12 pages.
Office Action of U.S. Appl. No. 13/858,038 dated Oct. 15, 2015, 12 pages.
Gircys, R. et al., "Movement Artefact Resistant Photoplethysmographic Probe", Elektronika Ir Elektrotechnika, IISN 1392-1215, vol. 20, No. 3, 2014, 4 pages.
Kuboyama, Yuta, "Motion Artifact Cancellation for Wearable Photoplethysmographic Sensor", B.S. Electrical Engineering and Computer Science, MIT, 2009, 66 pages.
Moharir, P.S. et al., "Optical Barker Codes", Electronics Letters, published May 2, 1974, vol. 10, No. 9, Mar. 28, 1974, 2 pages.
Office Action of U.S. Appl. No. 14/851,753 dated Sep. 27, 2016, 95 pages.
German Search Report of DE 102016207052.5 dated Mar. 1, 2017, 9 pages.
Office Action of U.S. Appl. No. 14/697,593 dated Nov. 24, 2017, 60 pages.
Nobata et al., Study of the Personal Authentication Technique Using ECG Signal toward Driver Recognition, 2 pages.
Office Action of U.S. Appl. No. 14/851,753 dated Mar. 22, 2017, 14 pages.
Office Action of U.S. Appl. No. 14/851,753 dated Dec. 21, 2016, 12 pages.
Office Action of U.S. Appl. No. 14/697,593 dated May 18, 2018, 21 pages.
Office Action of U.S. Appl. No. 14/961,277 dated Jun. 15, 2018, 8 pages.
Extended European Search Report of related application No. EP 15811941.2 dated Aug. 3, 2018, 7 pages.
Office Action of U.S. Appl. No. 15/656,595 dated Oct. 2, 2018, 143 pages.
Office Action of U.S. Appl. No. 15/720,489 dated Oct. 1, 2018, 146 pages.

\* cited by examiner

SYSTEM AND METHOD FOR CAPTURING AND DECONTAMINATING PHOTOPLETHYSMOPGRAPHY (PPG) SIGNALS IN A VEHICLE

The application is a continuation-in-part of, and claims priority to, U.S. application Ser. No. 14/697,593, filed on Apr. 27, 2015, the entire application of which is incorporated herein by reference; U.S. application Ser. No. 14/697,593 is a continuation-in-part of, and claims priority to, U.S. application Ser. No. 13/858,038, filed on Apr. 6, 2013, now issued as U.S. Pat. No. 9,272,689, the entire application of which is also incorporated herein by reference.

BACKGROUND

Photoplethysmography (PPG) provides a non invasive optical technique to detect changes in blood volume and blood composition in a biological being. However, PPG readings are susceptible to contamination by noise in the form of motion artifacts that can impact the usefulness of PPG data for biometric interpretation. Specifically, within a vehicle environment, motion artifacts can be enhanced based on noise, road vibration, individual movement, vehicle movement, inertial movement, among others. Motion artifacts become an exceptional property of captured PPG signals that pollute PPG readings and provide a skewed biometric interpretation.

BRIEF DESCRIPTION

According to one aspect, a computer implemented method for processing photoplethysmography (PPG) signals in a vehicle includes receiving a PPG waveform signal from an optical sensor. The method also includes processing a PPG measurement signal based on the PPG waveform signal. The method additionally includes receiving a noise waveform signal from at least one of: a seat assembly sensor, a vehicle sensor, and a vehicle system. Additionally, the method includes processing a motion artifacts measurement signal based on the noise waveform signal. The method further includes processing a refined PPG signal to suppress the motion artifacts measurement signal from the PPG measurement signal.

According to a further aspect, a system for processing photoplethysmography (PPG) signals in a vehicle includes a computing device that includes a processor. The system also includes a PPG determinant module that is included as a module of the computing device that receives a PPG waveform signal from an optical sensor and processes a PPG measurement signal based on the PPG waveform signal. Additionally, the system includes a motion artifact determinant module that is included as a module of the computing device that receives a noise waveform signal from at least one of: a seat assembly sensor, a vehicle sensor, and a vehicle system and processes a motion artifacts measurement signal based on the noise waveform signal. The system further includes a PPG signal filtering module that is included as a module of the computing device that processes a refined PPG signal to suppress the motion artifacts measurement signal from the PPG measurement signal.

According to still another aspect, a computer readable medium a computer readable medium including instructions that when executed by a processor executes a method for processing photoplethysmography (PPG) signals in a vehicle includes receiving a PPG waveform signal from an optical sensor. The method also includes processing a processing a PPG measurement signal based on the PPG waveform signal. The method additionally includes receiving a noise waveform signal from at least one of: a seat assembly sensor, a vehicle sensor, and a vehicle system. Additionally, the method includes processing a motion artifacts measurement signal based on the noise waveform signal. The method further includes processing a refined PPG signal to suppress the motion artifacts measurement signal from the PPG measurement signal.

DETAILED DESCRIPTION

Figure 1:
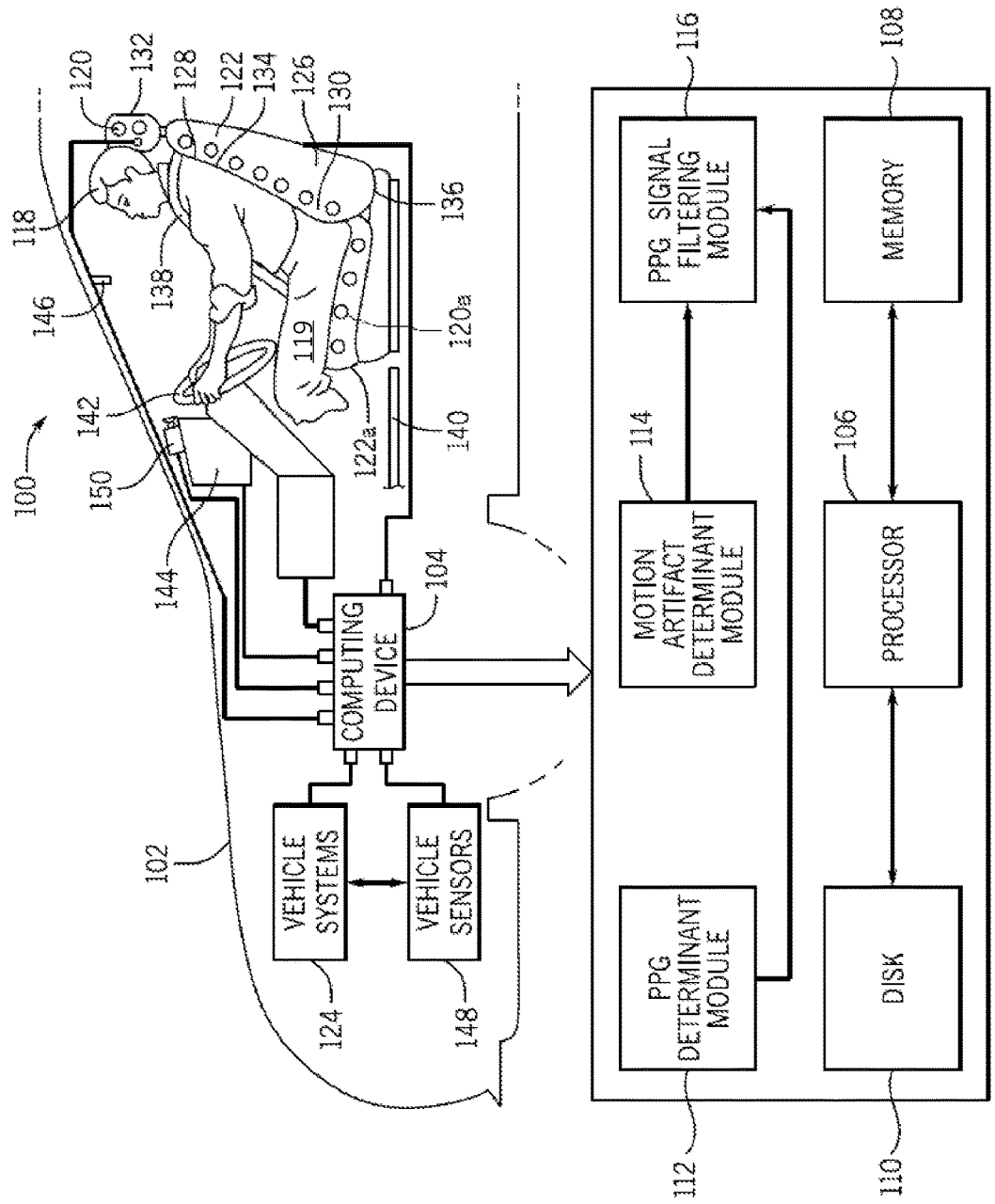
FIG. 1 is a schematic view of an operating environment for implementing systems and methods for capturing and decontaminating PPG signals in a vehicle according to an exemplary embodiment.

The following includes definitions of selected terms employed herein. The definitions include various examples and/or forms of components that fall within the scope of a term and that can be used for implementation. The examples are not intended to be limiting.

A "bus", as used herein, refers to an interconnected architecture that is operably connected to other computer components inside a computer or between computers. The bus can transfer data between the computer components. The bus can be a memory bus, a memory controller, a peripheral bus, an external bus, a crossbar switch, and/or a local bus, among others. The bus can also be a vehicle bus that interconnects components inside a vehicle using protocols such as Media Oriented Systems Transport (MOST), Controller Area network (CAN), Local Interconnect Network (LIN), among others.

"Computer communication", as used herein, refers to a communication between two or more computing devices (e.g., computer, personal digital assistant, cellular telephone, network device) and can be, for example, a network transfer, a file transfer, an applet transfer, an email, a hypertext transfer protocol (HTTP) transfer, and so on. A computer communication can occur across, for example, a wireless system (e.g., IEEE 802.11), an Ethernet system (e.g., IEEE 802.3), a token ring system (e.g., IEEE 802.5), a local area network (LAN), a wide area network (WAN), a point-to-point system, a circuit switching system, a packet switching system, among others.

A "disk", as used herein can be, for example, a magnetic disk drive, a solid state disk drive, a floppy disk drive, a tape drive, a Zip drive, a flash memory card, and/or a memory stick. Furthermore, the disk can be a CD-ROM (compact disk ROM), a CD recordable drive (CD-R drive), a CD rewritable drive (CD-RW drive), and/or a digital video ROM drive (DVD ROM). The disk can store an operating system that controls or allocates resources of a computing device.

A "database", as used herein can refer to table, a set of tables, a set of data stores and/or methods for accessing and/or manipulating those data stores. Some databases can be incorporated with a disk as defined above.

A "memory", as used herein can include volatile memory and/or non-volatile memory. Non-volatile memory can include, for example, ROM (read only memory), PROM (programmable read only memory), EPROM (erasable PROM), and EEPROM (electrically erasable PROM). Volatile memory can include, for example, RAM (random access memory), synchronous RAM (SRAM), dynamic RAM (DRAM), synchronous DRAM (SDRAM), double data rate SDRAM (DDR SDRAM), and direct RAM bus RAM (DRRAM). The memory can store an operating system that controls or allocates resources of a computing device.

A "module", as used herein, includes, but is not limited to, non-transitory computer readable medium that stores instructions, instructions in execution on a machine, hardware, firmware, software in execution on a machine, and/or combinations of each to perform a function(s) or an action(s), and/or to cause a function or action from another module, method, and/or system. A module may also include logic, a software controlled microprocessor, a discrete logic circuit, an analog circuit, a digital circuit, a programmed logic device, a memory device containing executing instructions, logic gates, a combination of gates, and/or other circuit components. Multiple modules may be combined into one module and single modules may be distributed among multiple modules.

An "operable connection", or a connection by which entities are "operably connected", is one in which signals, physical communications, and/or logical communications can be sent and/or received. An operable connection can include a wireless interface, a physical interface, a data interface and/or an electrical interface.

A "processor", as used herein, processes signals and performs general computing and arithmetic functions. Signals processed by the processor can include digital signals, data signals, computer instructions, processor instructions, messages, a bit, a bit stream, or other means that can be received, transmitted and/or detected. Generally, the processor can be a variety of various processors including multiple single and multicore processors and co-processors and other multiple single and multicore processor and co-processor architectures. The processor can include various modules to execute various functions.

A "portable device", as used herein, is a computing device typically having a display screen with user input (e.g., touch, keyboard) and a processor for computing. Portable devices include, but are not limited to, handheld devices, mobile devices, smart phones, laptops, tablets and e-readers. In some embodiments, a "portable device" could refer to a remote device that includes a processor for computing and/or a communication interface for receiving and transmitting data remotely.

A "vehicle", as used herein, refers to any moving vehicle that is capable of carrying one or more human occupants and is powered by any form of energy. The term "vehicle" includes, but is not limited to: cars, trucks, vans, minivans, SUVs, motorcycles, scooters, boats, go-karts, amusement ride cars, rail transport, personal watercraft, and aircraft. In some cases, a motor vehicle includes one or more engines. Further, the term "vehicle" can refer to an electric vehicle (EV) that is capable of carrying one or more human occupants and is powered entirely or partially by one or more electric motors powered by an electric battery. The EV can include battery electric vehicles (BEV) and plug-in hybrid electric vehicles (PHEV). The term "vehicle" can also refer to an autonomous vehicle and/or self-driving vehicle powered by any form of energy. The autonomous vehicle may or may not carry one or more human occupants. Further, the term "vehicle" can include vehicles that are automated or non-automated with pre-determined paths or free-moving vehicles.

A "vehicle system", as used herein can include, but is not limited to, any automatic or manual systems that can be used to enhance the vehicle, driving and/or safety. A "vehicle system", as used herein can include, but is not limited to, any automatic or manual systems that can be used to enhance the vehicle, driving and/or safety. Exemplary vehicle systems include, but are not limited to: an electronic stability control system, an anti-lock brake system, a brake assist system, an automatic brake prefill system, a low speed follow system, a cruise control system, a collision warning system, a collision mitigation braking system, an auto cruise control system, a lane departure warning system, a blind spot indicator system, a lane keep assist system, a navigation system, a transmission system, brake pedal systems, an electronic power steering system, visual devices (e.g., camera systems, proximity sensor systems), a climate control system, an electronic pretensioning system, a monitoring system, a passenger detection system, a vehicle suspension system, a vehicle seat configuration system, a vehicle cabin lighting system, an audio system, a sensory system, among others.

A "wearable computing device", as used herein can include, but is not limited to, a computing device component (e.g., a processor) with circuitry that can be worn by and/or in possession of a user. In other words, a wearable computing device is a computer that is subsumed into the personal space of a user. Wearable computing devices can include a display and can include various sensors for sensing and determining various parameters associated with a user. For example, location, motion, and biosignal (physiological) parameters, among others. Some wearable computing devices have user input and output functionality. Exemplary wearable computing devices can include, but are not limited to, watches, glasses, clothing, gloves, hats, shirts, jewelry, rings, earrings necklaces, armbands, shoes, earbuds, headphones and personal wellness devices.

I. System Overview

Referring now to the drawings, wherein the showings are for purposes of illustrating one or more exemplary embodiments and not for purposes of limiting the same, FIG. 1 illustrates a system 100 for implementing systems and methods for capturing and decontaminating photoplethysmography (PPG) signals in a vehicle according to an exemplary embodiment. The system 100 illustrated in FIG. 1 can be implemented within a vehicle 102. It is to be appreciated that the components of the system 100, as well as the components of other systems and architectures discussed herein, can be combined, omitted or organized into different architectures for various embodiments. It is also to be appreciated, that other components not shown in FIG. 1, (e.g., a display device, communication units/gateways, communication networks, and buses) or several instances of the components shown in FIG. 1 can also be included.

The system 100 can be implemented alone or in combination with a computing device 104 (e.g., controller, a head unit, etc.). The computing device 104 includes a processor 106, a memory 108, and a disk 110 which are operably connected for computer communication via a bus (not shown) and/or other wired and wireless technologies.

The computing device 104 can execute software serving to monitor and supervise various parameters of the engine (not shown) of the vehicle 102, as well as other components or systems of the vehicle 102. For example, the computing device 104 is capable of receiving signals from components of the vehicle 102 including sensors and devices. Signals output from sensors and devices can be sent to the computing device 104 and can be stored on the memory 108 and/or the disk 110. Further, the computing device 104 can facilitate information transfer between components of the vehicle 102 and/or control of the components of the vehicle 102. Both real-time and electronically stored signals can be processed by the processor 106 in accordance with software stored on the memory 108 and/or the disk 110.

In some embodiments, the computing device 104 can process signal output by sensors and devices into data formats that include values and levels. Such values and levels can include, but are not limited to, a numerical or other kind of value or level such as a percentage, a non-numerical value, a discrete state, a discrete value, a continuous value, among others. For example, in some cases, the value or level of X can be provided as a percentage between 0% and 100%. In other cases, the value or level of X can provided as a value in the range between 1 and 10. In still other cases, the value or level of X may not be a numerical value, but could be associated with a determined state, such a driving state.

In an exemplary embodiment, the computing device 104 also includes a PPG determinant module 112, a motion artifact determinant module 114, and a PPG signal filtering module 116. As will be described in more detail below, the PPG determinant module 112 communicates with one or more components of the vehicle 102 in order to process a PPG measurement signal (illustrated in FIG. 2B) that is associated with a driver 118 of the vehicle 102. The motion artifact determinant module 114 communicates with one or more sensors disposed at different locations of the vehicle 102 to determine a motion artifacts waveform that represents motion artifacts that are caused in part by the driver 118 and/or the vehicle 102 in the form of a motion artifacts measurement signal (illustrated in FIG. 2B). Additionally, the PPG signal filtering module 116 can communicate with the PPG determinant module 112 and the motion artifact determinant module 114 to receive the PPG measurement signal and the motion artifacts measurement signal in order to process a refined PPG signal (illustrated in FIG. 2B). As described in more detail below, the PPG signal filtering module 116 can process the refined PPG signal that is decontaminated from motion artifacts. The computing device 104 can utilize the refined PPG signal to determine biometric data and/or a driver state that is associated with the driver 118.

In the illustrated embodiment of FIG. 1, the system 100 also includes a sensor assembly 120 that is mechanically coupled to a vehicle seat 122 (e.g., driver's side vehicle seat). It is to be appreciated that the system and method discussed herein can be implemented with any number of sensor assemblies 120. Although, some embodiments discussed herein refer to the sensor assembly 120, it will be appreciated that a plurality of sensor assemblies 120 can be mechanically coupled to the vehicle seat 122.

The sensor assembly 120 can include one or more sensor assembly sensors (not all individually shown) that can include contact sensors and/or non contact sensors. The plurality of sensor assembly sensors can include electric current/potential (e.g., proximity sensors, inductive, capacitive), ultrasonic (e.g., piezoelectric, electrostatic), vibration, optical, vision, photoelectric or oxygen sensors, among others. It is appreciated that the one or more sensor assembly sensors are operable to sense a measurement of data associated with the driver 118, the vehicle 102, the vehicle environment, one or more vehicle systems 124, and/or occupants of the vehicle 102, and can output one or more data signals indicating one or more measurements of data to the computing device 104. The computing device 104 can convert the data signals into other data formats in order to generate other data metrics and parameters such as values and levels, as described above.

In an exemplary embodiment, one or more specific sensor assembly sensors can include an optical sensor (illustrated in FIG. 2A) for sensing PPG signals and additional signals to determine the driver's physiological state and/or motion artifacts associated with the driver 118 and/or vehicle 102, as described in more detail below. The sensor assembly sensors can additionally include, but are not limited to, a pressure sensor, an accelerometer, and physiological sensors. In some embodiments, the physiological sensors can include, but are not limited to, electric current/potential sensors, proximity sensors, optical sensors, visual sensors, sonic sensors, and additional photoelectric sensors using optics and light (e.g., infrared). The sensor assembly sensors can provide various types of physiological data that can be evaluated by the computing device 104 to determine the physiological state of the driver 118. Various types of physiological data that can be received from the sensor assembly sensors include, but are not limited to, heart information, such as, heart rate, blood pressure, blood flow, oxygen content, blood alcohol content (BAC), brain information, such as, functional near infrared spectroscopy (fNIRS), respiration rate information, as well as other kinds of information related to the autonomic nervous system or other biological systems of the driver 118.

As shown within the embodiment of FIG. 1, the vehicle seat 122 can be presented with the plurality of sensor assemblies 120 that are mechanically coupled to the vehicle seat 122 at various locations (shown as circular components disposed within the vehicle seat 122). However, it is to be appreciated, that in various embodiments, one or more sensor assemblies 120 can be disposed at different areas of the vehicle seat 122 that may not be illustrated in the exemplary embodiment of FIG. 1. For example, the plurality of sensor assemblies 120 can be disposed at a rear portion 126 of the vehicle seat 122, a front portion 128 of the vehicle seat 122, and (inner) side portions 130 of the vehicle seat 122.

In an exemplary embodiment, the vehicle seat 122 can include a headrest 132, a seat back 134, and a seat base 136, although other configurations of the vehicle seat 122 are contemplated. As shown in the illustrated embodiment of FIG. 1, the plurality of sensor assemblies 120 can be mechanically coupled to the vehicle seat 122 as disposed within the headrest 132, the seat back 134, and the seat base 136. It is understood that the plurality of sensor assemblies 120 can have any number of assemblies (e.g., two, three or more) and can be positioned in different locations and configurations within the vehicle seat 122. In some embodiments, the plurality of sensor assemblies 120 are positioned in locations determined to be best suited for sensing physiological data, contact-based surface motion data, and/or non-contact based motion data that is associated with the driver 118.

In one or more embodiments, the plurality of sensor assemblies 120 disposed within the vehicle seat 122 can be mechanically coupled to a common structural coupling material that allows for distribution of noise (e.g., engine noise, road noise, road vibration, driver movement, etc.) equally to all of the sensor assemblies 120. The mechanical coupling of the plurality of sensor assemblies 120 can reduce the effects of motion artifacts, since artifacts are distributed to impact each of the sensor assemblies 120 equally.

In some embodiments, the plurality of sensor assemblies 120 can be disposed in any portion of the vehicle 102. For example, a seat belt 138, floor board 140, steering wheel 142, dashboard 144, rear-view mirror 146, etc. can include one or more sensor assemblies 120 that include different types of sensor assembly sensors (e.g., optical, visual, capacitive sensors, electrodes, etc.). Moreover, in some cases, one or more sensor assemblies 120 can be included within one or more wearable devices (not shown) worn by the driver 118. The wearable devices can include, but are not limited to, wearable rings, watches, eye glasses, and articles of clothing. In other embodiments, one or more sensor assemblies 120 can be included with a portable device (not shown) located in proximity to the driver 118 such as a smart phone or similar device, or associated with an article of clothing worn by the driver 118.

In one embodiment, at least one of the plurality of sensor assemblies 120 may be disposed on the left front side of vehicle seat 122, for example, sensor 120a. This location may be best suited to receive the highest amount of contact with the driver's left leg 119. The left leg 119 is typically moved less than the right leg since the right leg is often used for the accelerator and brake pedals. The less movement of the leg, the less noise imparted to the sensor 120a. In one exemplary embodiment, the sensor 120a may be located between about 10 centimeters and about 30 centimeters from the front edge 122a of the vehicle seat 122 and between about 10 centimeters and about 30 centimeters from the left edge 122b of the vehicle seat 122. In another embodiment, the sensor 120a may be located between about 20 centimeters and about 25 centimeters from the front edge 122a and between about 15 centimeters and about 20 centimeters from the left edge 122b.

The vehicle 102 can additionally include the one or more vehicle sensors 148. The vehicle sensors 148 can include sensors associated with one or more vehicle systems 124 and/or other components of the vehicle 102. The vehicle sensors 148 can sense and measure a stimulus (e.g., a signal, a property, a measurement, or a quantity) associated with the vehicle 102 and/or one or more particular vehicle systems 124. In some embodiments, the vehicle sensors 148 can also sense and measure a stimulus associated with the driver 118, as described in more detail below. The vehicle sensors 148 can output one or more data signals representing one or more stimulus from the vehicle sensors 148. The vehicle sensors 148 can be disposed at various locations within a passenger cabin of the vehicle 102, including, but not limited to a head unit (not shown), the floor board 140, the dashboard 144, etc. Additionally, vehicle sensors 148 can be located at exterior portions of the vehicle 102 such as side view mirrors (not shown), door panels (not shown), front and rear bumpers (not shown), vehicle wheels (not shown), vehicle engine (not shown), etc.

In particular, the one or more vehicle sensors 148 (not all individually shown) can include, but are not limited to, an accelerometer, a magnetometer, a gyroscope, an ambient light sensor, a proximity sensor, a global positioning sensor system, a lateral acceleration sensor, and the like. Additionally, vehicle sensors 148 can include, but are not limited to a vehicle speed sensor, a steering angle sensor, accelerator pedal sensor, a brake sensor, a throttle position sensor, a wheel sensor, a camshaft sensor, an electronic parking sensor, among others. The vehicle sensors 148 can also include visual sensors in the form of cameras 150 mounted to the interior of the vehicle 102 and cameras, radar sensors, and laser sensors mounted to the exterior of the vehicle 102. Further, vehicle sensors 148 can include sensors located external to the vehicle 102 and accessed, for example, via a network. These sensors can include external cameras, radar and laser sensors on other vehicles in a vehicle-to-vehicle network, street cameras, surveillance cameras, blind spot indicator system, lane keep assist system, among others.

In an exemplary embodiment, one or more vehicle systems 124 (not all individually shown), discussed above can include, a data storage mechanism (e.g., memory) for storing data utilized by said vehicle systems 124, for example, sensitive data such as contact data, route data, password data, driver behavior profiles, driver physiological data profiles, among others.

The vehicle sensors 148 and vehicle systems 124 can provide vehicle data to the computing device 104 that can be utilized to determine various metrics with respect to the driver 118 and the vehicle 102. Specifically, vehicle data can include driver and/or vehicle conditions, states, statuses, behaviors, and associated information. As discussed in detail below, in an exemplary embodiment, the vehicle sensors 148 and vehicle systems 124 can capture one or more artifacts and can output respective signals that are associated with the movement of the driver 118 and/or the vehicle 102.

II. Processing a PPG Measurement Signal Associated with the Driver

Referring again to FIG. 2A, a schematic view of an optical sensor 202 is illustrated according to an exemplary embodiment. As discussed above, one or more of the sensor assemblies 120 includes the optical sensor 202. The optical sensor 202 can be configured to emit a plurality of light sources (near-Infrared, Infrared, laser, etc.) at a plurality of frequencies to capture and measure various signals that represents physiological data associated to the driver 118. The optical sensor 202 is also configured to increase or decrease an intensity of light emitted from the plurality of light sources in order to emit a plurality of wavelengths based on the location of the optical sensor 202 and the type of measurement that is output by the optical sensor 202.

In an exemplary embodiment, one or more optical sensors 202 are configured to emit a near-infrared or infrared LED light source in order to read and measure PPG signals of the driver 118 and/or occupants of the vehicle 102. The one or more optical sensors 202 can be configured to provide a volumetric measurement of the driver's blood volume and blood composition to determine metrics relating to the driver's blood oxygen levels that can have an effect on the driver's heart rate. Specifically, the one or more optical sensors 202 can utilize pulse oximetry that provides a reflected PPG measurement of the absorption of various wavelengths of infrared or near-infrared light by tissue within the driver's body. The one or more optical sensors 202 can each measure the amount of light that is reflected by the tissue in order to determine an amount of light that is absorbed by the driver's body. In other words, the optical sensors 202 can measure the pulsation change in the driver's blood volume with respect to oxygen saturation as more blood will absorb a higher amount of light, and less blood will absorb a lesser amount of light.

In an exemplary embodiment, each optical sensor 202 is located within one or more sensor assemblies 120 that are disposed within the (driver's) vehicle seat 122 and other locations within the vehicle cabin. The plurality of sensor assemblies 120 can be specifically positioned in areas that are situated to contact or not contact the surface of the driver's skin and/or clothing in order for the optical sensors 202 to clearly measure the driver's PPG signals. For example, one or more sensor assemblies 120 can be disposed at areas of the vehicle seat 122 and/or the vehicle 102 that are located near areas of the driver's body that have thinner layers of skin (e.g., ear lobes, finger tips). Additionally, one or more sensor assemblies 120 may be disposed at areas that are near areas of the driver's body that have thick blood vessels (e.g., back, thighs).

In one embodiment, the optical sensor 202 can include source circuitry 204 and detector circuitry 206. Specifically, the source circuitry 204 can include the near-infrared or infrared LED light source and/or a laser light source, etc. that emits light toward various areas of the driver's body as the driver 118 is seated within the vehicle seat 122. More particularly, the source circuitry 204 can include a plurality of LED and laser light sources (not shown) that are configured to provide various light colors and intensities. For example, the plurality of LED light sources can emit light with different wavelengths (e.g., 660-1600 nm) and different frequencies (430 THz-300 GHz) that illuminate through the driver's skin. The source circuitry 204 of each of the optical sensors 202 can be configured to increase or decrease the intensity of emitted light in order to emit a plurality of wavelengths based on the location of the optical sensor(s) 202 and the type of measurement that is being output by the optical sensor(s) 202. For example, with respect to the location of the optical sensors 202, the source circuitry 204 can utilize shorter wavelengths of light at areas where the optical sensors 202 are located that emit light where the driver 118 is expected to be wearing clothing (e.g., back, sides) as oppose to areas where light can typically be emitted directly to the driver's skin (e.g., neck, hands). In some embodiments, the source circuitry 204 can calibrate the intensity of various types of light by initially emitting less intense longer wavelengths that can be used to capture one or more measurements such as PPG signals on skin. The source circuitry 204 can then incrementally modify the intensity of the light wavelengths in order to penetrate through the driver's clothing to allow for the interrogation of blood vessels. In some embodiments, the intensity of light can also be influenced by the opacity of the driver's skin. For example, the effect of the driver's skin color can be utilized as a factor to modify the intensity of the LED light source during calibration by the source circuitry 204.

In one or more embodiments, the detector circuitry 206 can include a photodiode that can be configured to read an amount of scattered light that is transmitted through blood perfused tissue and measured on the opposite side of the tissue as the light provided by the source circuitry 204 and/or reflected back to the same side of the tissue as the light provided by the source circuitry 204. In some embodiments, the detector circuitry 206 can include one or more cameras (in lieu of or in addition to the photodiode) that are configured to capture images in order to analyze and provide measurements with respect to the transmitted light and/or the reflected light. In some configurations, the detector circuitry 206 can be positioned in order to measure one or more paths of light from the light source(s) of the source circuitry 204 that reflects back the source circuitry 204. Upon reading the amount of scattered light that is reflected back to the detector circuitry 206, each optical sensor 202 can provide a representation of its reading in the form of one or more PPG waveform signals. In alternate configurations, the detector circuitry 206 can be positioned in order to measure one or more paths of light from the light source(s) of the source circuitry 204 that pass through the tissue. Upon reading the amount of scattered light that passes through the tissue to the detector circuitry 206, each optical sensor 202 can provide a representation of its reading in the form of one or more PPG waveform signals.

In an exemplary embodiment, one or more optical sensors 202 can each output a respective PPG waveform signal (not shown) to the PPG determinant module 112 within a predetermined frequency of time (e.g., 10 ms). Each PPG waveform signal output by each of the optical sensors 202 can include a plurality of signal segments (not shown). The signal segments can include the measurement of PPG signals of the driver 118 along with artifacts caused by driver and vehicle movement that have an effect on the reading of the PPG signals by the optical sensor 202. Accordingly, in some situations, the PPG waveform signals output by the one or more of optical sensors 120 can be contaminated by the artifacts and can provide skewed PPG signals. Additionally, each PPG waveform signal can include signal features (not shown) such as signal peaks that can be further evaluated to determine PPG signal measurements and noise measurements. Additional signal features that can be evaluated include frequency, time duration, wave amplitude, among others. It is appreciated that other characteristics of the PPG waveform signal can also be identified as a signal feature.

Figure 2A:
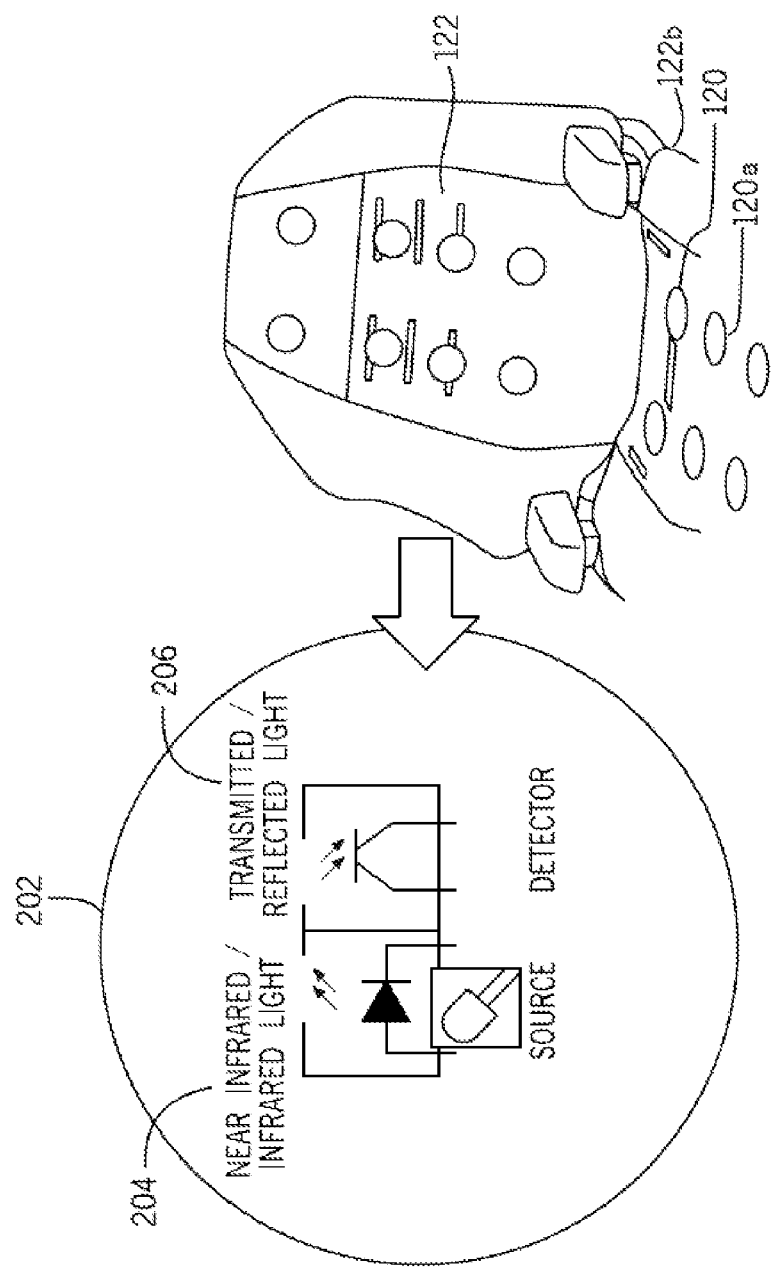
FIG. 2A is a schematic view of an optical sensor according to an exemplary embodiment.
Figure 2B:
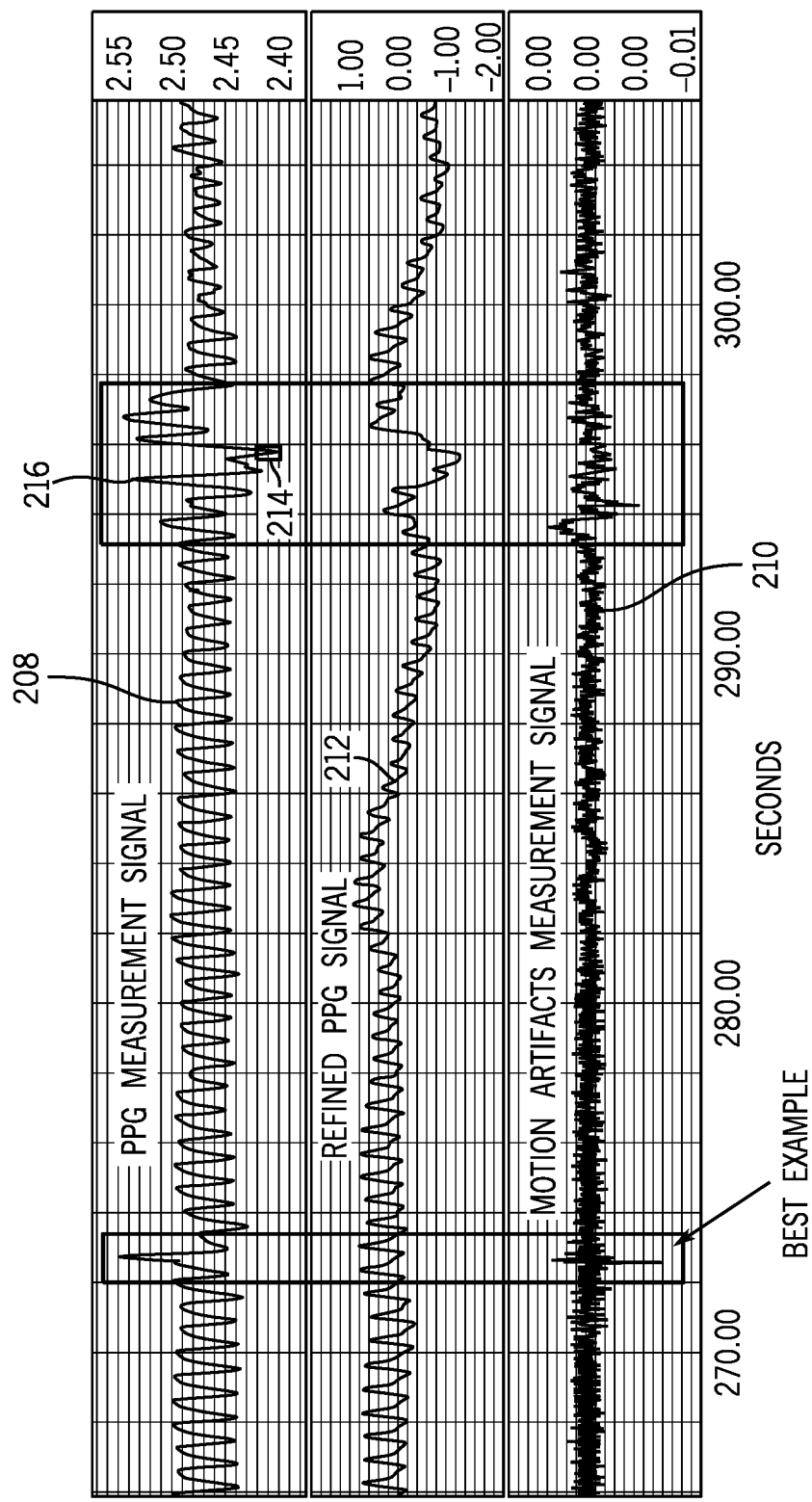
FIG. 2B is a schematic representation of an exemplary PPG measurement signal, a noise measurement signal, and a refined PPG signal according to an exemplary embodiment.

FIG. 2B is a schematic representation of an exemplary PPG measurement signal 208, a noise measurement signal 210 (e.g., a motion artifacts measurement signal), and a refined PPG signal 212 according to an exemplary embodiment illustrates an exemplary PPG measurement signal 208. The PPG determinant module 112 can utilize various methods to process the PPG measurement signal 208 that can include an aggregated measurement of the driver's blood volume and blood composition. Processing completed by the PPG determinant module 112 generally includes converting a single PPG waveform signal or aggregating a plurality of PPG waveform signals into the PPG measurement signal 208. Processing can include amplification, mixing, and filtering of the plurality of PPG waveform signals, as well as other signal processing techniques known in the art (discussed in more detail below).

Each PPG measurement signal 208 can include a plurality of signal segments 214 (only one signal segment 214 is shown). It is to be appreciated that one or more signal segments 214 can include any size and/or portion of the PPG measurement signal 208. The signal segments 214 can include the measurement of PPG signals of the driver 118 (compiled from one or more PPG waveform signals) along with artifacts caused by driver and vehicle movement. Additionally, each PPG measurement can include signal features such as signal peaks 216 that can be further evaluated to determine PPG signal measurements and noise measurements. Additional signal features that can be evaluated include frequency, time duration, wave amplitude, local maximum and minimum points, and inflection points (related to the second derivative of PPG) among others (not shown). It is appreciated that other characteristics of the PPG measurement signal 208 can also be identified as a signal feature.

Figure 3:
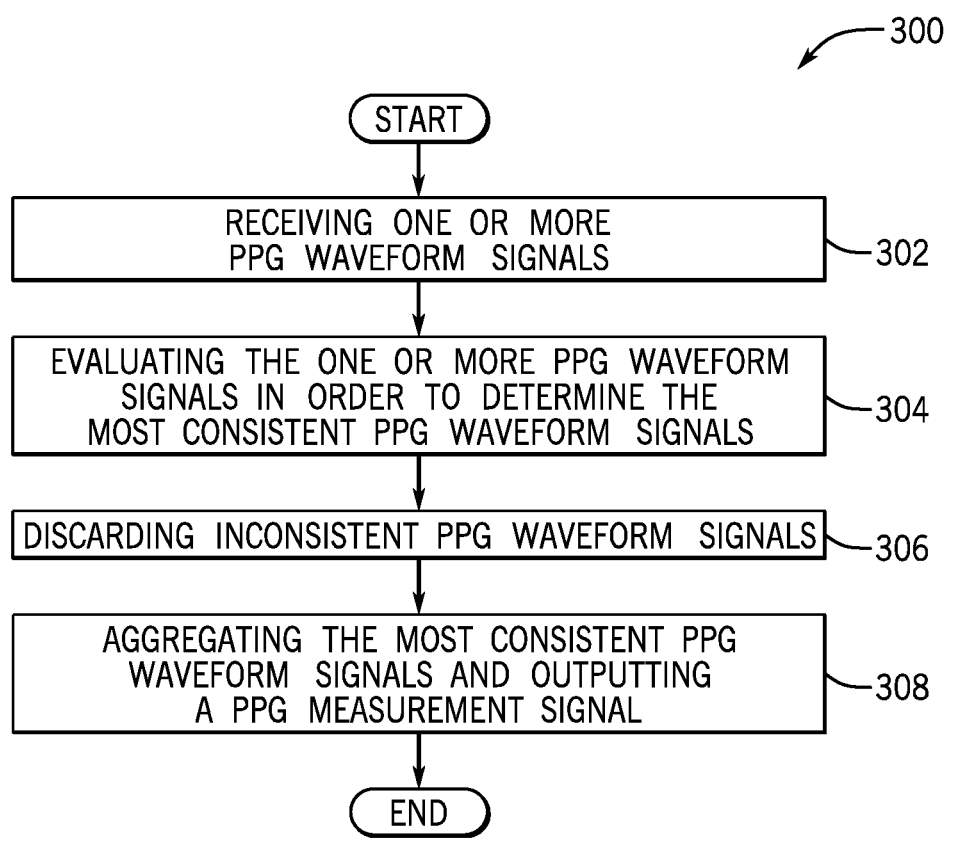
FIG. 3 is a process flow diagram of an exemplary method for processing a PPG measurement signal from one or more PPG waveform signals from the operating environment of FIG. 1 according to an exemplary embodiment.

Referring now to FIG. 3, a process flow diagram of an exemplary method 300 for processing a PPG measurement signal 208 from the one or more PPG waveform signals is shown according to an exemplary embodiment. FIG. 3 will be described with reference to the systems/components/illustrations of FIG. 1, FIG. 2A, and FIG. 2B, though it is to be appreciated that the method of FIG. 3 can be used with other systems/components. In some embodiments, some or all of the steps of the method 300 can be preformed by the PPG determinant module 112. In other embodiments, other modules can perform some or all of the steps described with the method 300.

At block 302, the method includes receiving one or more PPG waveform signals. In one embodiment, the PPG determinant module 112 communicates with one or more sensor assemblies 120 that are disposed at various areas of the vehicle seat 122 and/or the vehicle 102 in order to receive the one or more PPG waveform signals that are output by the one or more of optical sensors 202. Upon receipt of the one or more PPG waveform signals, the PPG determinant module 112 can store data pertaining to the signal features of the one or more PPG waveform signals onto the memory 108 and/or the disk 110 of the computing device 104 in order to be further evaluated.

At block 304, the method includes evaluating the one or more PPG waveform signals in order to determine the most consistent PPG waveform signals. In one embodiment, the PPG determinant module 112 accesses data pertaining to the signal features of the one or more PPG waveform signals from the memory 108 and/or the disk 110 and can determine one or more PPG waveform signals that include similar waveform patterns based on one or more signal features that are within one or more determined mean signal feature categories. More specifically, the PPG determinant module 112 can evaluate signal features of each of the PPG waveform signals including frequency, time duration, wave amplitude, measurement between signal peaks, local maximum and minimum points, and inflection points (related to the second derivative of PPG), etc. Upon evaluating the signal features, the PPG determinant module 112 can determine measurement values associated with each of the signal features (e.g., distance/time measurements) in order to compute mean values associated to each of the signal features.

Upon determining mean values associated to each of the signal features, the PPG determinant module 112 can determine one or more signal feature categories associated with each of the signal features. The one or more signal feature categories can include a categorization of the signal features of the one or more PPG waveform signals that are within a predetermined range from the mean signal feature value. For example, a mean signal feature category can include a peak signal measurement category that includes a predetermined range of values that are within a range from a mean value of a measurement between peak signals of each of the plurality of waveform signals. The PPG determinant module 112 can further evaluate PPG waveform signals that include signal features that fall within a predetermined amount of signal feature categories in order to determine the most consistent PPG waveform signals. It is to be appreciated that the PPG determinant module 112 can utilize various other methods to evaluate the one or more PPG waveform signals in order to determine the most consistent PPG waveform signals By determining the most consistent PPG waveform signals, the PPG determinant module 112 can capture the most accurate representation of the driver's PPG signals that have been captured from the vehicle seat 122 and/or the vehicle 102. For example, the PPG determinant module 112 can evaluate ten PPG waveform signals provided by ten optical sensors 202 in order to determine three PPG waveform signals that include signal features that include values that fall within the predetermined amount of signal feature categories.

At block 306, the method includes discarding inconsistent PPG waveform signals. In one embodiment, the PPG determinant module 112 removes the inconsistent PPG waveform signals stored on the memory 108 and/or the disk 110 in order ensure such data does not influence the measurement of the driver's PPG signals. Specifically, the PPG determinant module 112 removes PPG waveform signals that are not determined to fall within the predetermined amount of signal feature categories. In particular, by discarding the inconsistent PPG signal waveforms 208 based on the evaluation conducted at block 304, the PPG determinant module 112 ensures that optical sensors 202 that are located in areas of the vehicle seat 122 and/or the vehicle 102 from which PPG readings may not have been completely or accurately captured are not accounted for when processing the PPG measurement signal 208.

At block 308, the method includes aggregating the most consistent PPG waveform signals and outputting a PPG measurement signal 208. In an exemplary embodiment, the PPG determinant module 112 aggregates the most consistent PPG waveform signals as determined at block 304 into the PPG measurement signal 208 that represents the most consistent measurement of the driver's PPG signals.

With reference again to FIG. 1, FIG. 2A, and FIG. 2B, in another embodiment, the PPG determinant module 112 can determine an optimum PPG waveform signal (not shown) that is selected out of the plurality of PPG waveform signals output by the plurality of optical sensors 202. The optimum PPG waveform signal can be determined by the PPG determinant module 112 to be the most accurate measurement of the driver's PPG signals. In one embodiment, the PPG determinant module 112 can determine the optimum PPG waveform signal by determining the PPG waveform signal that is output by the optical sensor 202 that emits the lowest amount of LED light intensity in order to capture the driver's PPG signals. In other words, the optimum PPG waveform signal is determined to be the PPG waveform signal that is most likely to be captured closer to the driver's skin, thereby ensuring minimal interference by the driver's clothing or the space between the sensor and the driver 118.

In another embodiment, the PPG determinant module 112 can determine the optimum PPG waveform signal by communicating with one or more pressure sensors included within the one or more sensor assemblies 120 in order to determine the pressure sensor that measures the highest pressure measurement caused by the driver 118 seated within the vehicle seat 122. In particular, one more sensor assemblies 120 that include the pressure sensor(s) can be disposed at particular locations of the vehicle seat 122 in which the change in pressure caused by the driver 118 is detected. The pressure sensor(s) can communicate pressure measurement data to the PPG determinant module 112 with respect to which pressure sensor measures the highest pressure measurement caused by the driver 118 in order to determine the optimum PPG waveform signal. In other words, the optimum PPG waveform signal is determined to be the PPG waveform signal that is most likely to be captured by an optical sensor 202 included within the sensor assembly 120 that is determined to be at a location of the vehicle seat 122 that is most utilized by the driver 118 (i.e., a location where a consistent/constant measurement can take place). Upon determining the optimum PPG waveform signal, the PPG determinant module 112 can convert the optimum PPG waveform signal into the PPG measurement signal 208.

In additional embodiments, the PPG determinant module 112 can process the PPG measurement signal 208 by separately evaluating PPG waveform signals that are captured from respective areas of the vehicle seat 122 in order to determine the optimum PPG waveform signal captured from each area of the vehicle seat 122. For example, the PPG determinant module 112 can determine four optimum PPG waveform signals captured by the optical sensors 202 located at the each of the seat back 134, and the seat base 136. Upon determining the optimum PPG waveform signals, the PPG determinant module 112 can aggregate the optimum PPG waveform signals captured from each area of the vehicle seat 122 into the PPG measurement signal 208. It is to be appreciated that the PPG determinant module 112 can utilize various other methods to process the PPG measurement signal 208 from one or more PPG waveform signals provided by the plurality of optical sensors 202.

As discussed above, the PPG waveform signals can be contaminated with motion artifacts caused by the driver 118 and/or the vehicle 102. Therefore, one or more signal segments 214 of the PPG measurement signal 208 that is processed by the PPG determinant module 112 also includes motion artifacts. Accordingly, the PPG determinant module 112 sends the processed PPG measurement signal 208 to the PPG signal filtering module 116 in order filter the motion artifacts and extract a refined PPG signal 212.

Apart from being configured to read and measure PPG signals of the driver 118, as discussed above, the plurality of optical sensors 202 can also emit a plurality of light sources at a plurality of frequencies in order to read signals that are associated with additional physiological data related to the driver 118 and/or occupants of the vehicle 102. For example, the optical sensors 202 can emit signals to determine physical information related to the driver 118 and/or occupants including biometric identification of the driver 118 and/or occupants based on sensing signals associated to physical characteristics (e.g., posture, position, movement) and biological characteristics (e.g., blood pressure, blood flow, oxygen content in the blood, etc.).

In one embodiment, the optical sensors 202 can emit the plurality of light sources at the plurality of frequencies in order to non invasively measure the driver's and/or occupant's blood alcohol levels. For example, the source circuitry 204 of the optical sensors 202 can emit light into the driver's skin. The optical sensors 202 can measure a tissue alcohol concentration based on the amount of light that is reflected back by the skin to the detector circuitry 206. Additionally, the optical sensors 202 can noninvasively monitor a condition of the driver 118 through the determination of biological signals, such as body-trunk plethysmograph and respiration that are detected from the driver's back from one or more optical sensors 202 included within sensor assemblies 120 disposed at the seat back 134 of the vehicle seat 122. In particular, one or more filtered signals can be evaluated to determine the driver's PPG signals that fall between normal and intoxicated states in order to determine driver intoxication. Such a technique is described by K. Murata, et. al in "Noninvasive Biological Sensor System for Detection of Drunk Driving," IEEE Transactions on Information Technology in Biomedicine, Vol. 15, No, 1, 2011, the entire contents of which are incorporated by reference.

In an additional embodiment, the optical sensor 202 can emit various light sources in order to non invasively identify the driver 118 and/or occupant(s) of the vehicle 102 via biometric identification. For example, one or more physiological signals (e.g., PPG signals, etc.) can be measured by the optical sensors 202 in order to determine physiological signals that can be matched against a database of enrolled biometric templates. The database of enrolled biometric templates can include a biometric template from the driver 118 and/or occupants of the vehicle 102. Examples of biometric identification techniques are described within the parent application of the present application. Additional, exemplary biometric techniques are described by A. Reşit Kaysaoğlu et. al in "A novel feature ranking algorithm for biometric recognition with PPG signals," Computer in Biology and Medicine, Vol. 49, 2014, 1-14, and as well as Agrafito et al. filed May 10, 2012, the entirety of both being hereby incorporated by reference.

III. Processing a Motion Artifacts Measurement Signal Associated with the Driver and the Vehicle Referring back to FIG. 1 and FIG. 2B, several techniques to determine motion artifacts associated to the driver 118 and the vehicle 102 will now be described. In an exemplary embodiment, the motion artifact determinant module 114 can communicate with one or more sensor assembly sensors, one or more vehicle sensors 148, and/or one or more vehicle systems 124 in order to determine motion artifacts associated with the driver 118 seated within the vehicle seat 122 and/or the vehicle 102 itself as it is being driven by the driver 118.

In an exemplary embodiment, data can be provided by various types of seat assembly sensors, vehicle sensors 148, and/or vehicle systems 124 in the form of one or more noise waveform signals (not shown) that are output within a predetermined frequency of time (e.g., 10 ms) to the motion artifact determinant module 114. As discussed below, the motion artifact determinant module 114 can convert one noise waveform signal or aggregate a plurality of noise waveform signals output by a plurality of sensor assembly sensors, vehicle sensors 148, and vehicle systems 124 into the motion artifacts measurement signal 210.

Some exemplary embodiments utilizing specific types of sensor assembly sensors, vehicle sensors 148, and vehicle systems 124 to determine motion artifacts associated with the driver 118 and the vehicle 102 will now be discussed below with reference to FIG. 1, FIG. 2A, and FIG. 2B. However, it is to be appreciated, that sensors not specifically disclosed within the exemplary embodiments discussed below may also be utilized alone or in combination with one another to determine the motion artifacts measurement signal 210.

In one or more embodiments, the optical sensor 202 can emit a blue/near UV visible light source that is configured to emit light towards the surface of the driver's skin. In particular, the blue/near UV visible light source can be configured to increase or decrease the intensity of emitted light in order to emit a plurality of wavelengths based on the location of the optical sensor 202 with respect to the driver 118. For example, the blue/near UV visible light source can emit a shorter wavelength of light at areas where the driver 118 is expected to be wearing clothing (e.g., back, sides) as oppose to areas where light can typically be transmitted directly to the driver's skin (e.g., neck, hands). The detector circuitry 206 of the optical sensor 202 can determine a reflectance of light that is absorbed by the surface of the driver's skin in order to determine the driver's movements within the vehicle seat 122. One or more optical sensors 202 can output one or more of noise waveform signals that are indicative of the driver's movements within the vehicle seat 122.

In one or more embodiments, seat assembly sensors including, but not limited to, accelerometers (not shown), gyroscopes (not shown), proximity detectors (not shown), magnetometers (not shown), etc., can be utilized alone or in combination to output one or more noise waveform signals to the motion artifact determinant module 114. In one embodiment, one or more accelerometers included within one or more sensor assemblies 120 can determine motion artifacts associated to the driver 118. In particular, the one or more accelerometers can communicate data that is indicative of the driver's movement within the vehicle seat 122. In some embodiments, the one or more accelerometers can be positioned atop the optical sensor 202, each oriented perpendicular to each other in order to capture motion artifacts that can most directly disturb the measurement of the driver's PPG signals by the optical sensor 202. Specifically, the one or more accelerometers can also include capacitive accelerometers that are used to determine and measure changes in a degree of movement of the driver 118 within the vehicle seat 122. For example, as the driver 118 accelerates and brakes the vehicle 102, the accelerometer(s) can determine a rate of change of the movement of the driver 118 as the driver 118 may shift back and forth within the vehicle seat 122.

Additionally, in some embodiments, the one or more pressure sensors included within the one or more sensor assemblies 120, discussed above, can be utilized to determine motion artifacts associated to the driver 118. In particular, one or more sensor assemblies 120 that include the pressure sensor(s) can be disposed at particular locations of the vehicle seat 122 in which the driver's movement can be determined based on the change in pressure as the driver 118 moves within the vehicle seat 122. The pressure sensor(s) can include hardware configured to determine movement of the driver 118 based on the change in pressure as detected by the shifting of the driver's weight within the vehicle seat 122. For example, one or more pressure sensors located within the seat back 134 of the vehicle seat 122 can determine and measure a change in movement of the driver 118 whose weight distributes away and toward the seat back 134 as the driver 118 moves forward or backward within the vehicle seat 122. The pressure sensor(s) can output one or more noise waveform signals to the motion artifact determinant module 114.

In an additional embodiment, one or more vibration sensors (not shown) included within the one or more sensor assemblies 120 and/or vehicle sensors 148 can also be utilized to determine motion artifacts associated to the driver 118 and/or the vehicle 102. The one or more vibration sensors can include piezoelectric sensors for detecting mechanical vibrations associated to the vehicle seat 122 and/or the vehicle 102. For example, the one or more vibration sensors can sense vibrations that can be attributed to the engine, the roadway on which the vehicle 102 is being driven, and/or the driver's movement within the vehicle seat 122. The vibration sensor(s) can output one or more noise waveform signals to the motion artifact determinant module 114.

In some embodiments, one or more proximity sensors (not shown) included within the one or more sensor assemblies 120 and/or vehicle sensors 148 can also be utilized to determine motion artifacts associated with the driver 118 and/or the vehicle 102. For example, a plurality of proximity sensors can be operable to determine the location of the driver 118 as he or she moves within the vehicle seat 122. Specifically, each proximity sensor can output a proximity measurement based on the proximity of the driver 118 to the respective sensor. The proximity sensor(s) can output one or more noise waveform signals to the motion artifact determinant module 114.

In an alternate embodiment, one or more wearable devices can be worn by the driver 118 that can also measure the driver's movement within the vehicle seat 122. The wearable device(s) can include one or more movement tracking sensors (e.g., accelerometer, gyroscope, etc.). The wearable device(s) can include device logic that is configured to track and measure movements of the driver 118 wearing the wearable device(s). The wearable device(s) can output one or more noise waveform signals to the motion artifact determinant module 114.

In some embodiments, the (internal) cameras 150 included as part of the vehicle sensors 148 can be located throughout the vehicle 102. Specifically, one or more cameras 150 can be positioned in various areas in front of, above, and/or around the vehicle seat 122 in order to capture real time images of the driver 118 as the vehicle 102 is being driven. The one or more cameras 150 can include hardware configured to interpret video or image data sensed by the camera(s) 150 to recognize any movement associated with the driver 118 within the vehicle seat 122. In one embodiment, the processor 106 can include camera logic that can evaluate image data output by one or more cameras 150 and can compile the image data to determine and measure changes in the movement of the driver 118 within the vehicle seat 122. The compiled data can be provided to the motion artifact determinant module 114 in the form of one or more noise waveform signals.

In one exemplary embodiment, the cameras 150, hardware and/or camera logic can evaluate the image data and/or video data to determine the position of the driver 118 within the vehicle seat 122. The position of the driver 118 can be provided to the PPG determinant module 112 in the form of position data. The position data can assist the PPG determinant module 112 in determining which sensor assembly 120 is likely to provide the optimum PPG waveform signal. In other words, the optimum PPG waveform signal is determined to be the PPG waveform signal that is most likely to be captured by an optical sensor 202 included within the sensor assembly 120 that is determined to be at a location of the vehicle seat 122 that is most utilized by the driver 118 (i.e., a location where a consistent/constant measurement can take place). Upon determining the optimum PPG waveform signal, the PPG determinant module 112 can convert the optimum PPG waveform signal into the PPG measurement signal 208. For example, if the driver 118 is leaning to the left then the sensor assemblies 120 and the optical sensors 202 on the left side of the vehicle seat 122 are likely to provide the optimum PPG waveform signal. The PPG determinant module 112 can then ignore the sensor assemblies on the right side of the vehicle seat 122.

In another exemplary embodiment, the cameras 150, hardware and/or camera logic can evaluate the image data and/or video data to determine the characteristics of the clothing worn by the driver 118. The characteristics can be provided to the source circuitry 204 in the form of characteristic data. The source circuitry 204 of each of the optical sensors 202 can be configured to increase or decrease the intensity of emitted light in order to emit a plurality of wavelengths based on the characteristic data. For example, the source circuitry 204 can utilize shorter wavelengths of light at areas where the optical sensors 202 are located where the driver 118 is wearing darker colored or thicker clothing, as opposed to areas where the driver 118 is wearing lighter colored or thinner clothing. In some embodiments, the source circuitry 204 can be calibrated to the characteristics of various types of clothing. The intensity of the emitted light can then be selected based on the characteristic data received from the cameras 150, hardware and/or camera logic and the calibration. In some embodiments, the intensity of light can also be influenced by the opacity of the driver's skin. For example, the effect of the driver's skin color in combination with the characteristic data of the clothing can be utilized as a factor to modify the intensity of the LED light source by the source circuitry 204.

Additional vehicle sensors 148 can be used in conjunction with one another to provide data regarding body movement of the vehicle 102 as the vehicle 102 is being driven on a roadway. For example, vehicle sensors 148 disposed at each wheel of the vehicle 102 can measure a ride level of the vehicle 102 and one or more accelerometers included as part of the vehicle sensors 148 can measure vertical body acceleration of the vehicle 102 in order to accurately measure road noise. The vehicle sensors 148 can also be used to determine the steering angle, roll, pitch, lateral acceleration and yaw of the vehicle 102 as an indication of the vehicle 102 reacting to turns, acceleration, braking, and road noise that can affect the capturing of one or more PPG signals by the optical sensors 202. For example, one or more vehicle sensors 148 that include the steering sensor, gyroscope, lateral acceleration sensors, acceleration pedal sensors, brake sensors, wheel speed sensors, etc. can be utilized alone or in combination with one another to output noise waveform signals to the motion artifact determinant module 114.

In some embodiments, one or more vehicle systems 124 can provide one or more noise waveform signals to the motion artifact determinant module 114. For example, the electronic stability control system (not shown) can monitor the yaw rate of the vehicle 102 and can output movement data in the form of a noise waveform signal.

In an exemplary embodiment, upon receiving one or more noise waveform signals from the sensor assembly sensors, vehicle sensors 148, and/or vehicle systems 124, the motion artifact determinant module 114 can process the one or more noise waveform signals into the motion artifacts measurement signal 210. Processing completed by the motion artifact determinant module 114 generally includes converting one noise waveform signal or aggregating the plurality of noise waveform signals into the motion artifacts measurement signal 210. Processing can include amplification, mixing, and filtering of one or more noise waveform signals, as well as other signal processing techniques known in the art. The motion artifacts measurement signal 210 can include signal segments (not shown) and signal features (not shown) similar to the PPG measurement signal 208 that are representative of motion artifacts associated with the driver 118 and the vehicle 102.

In some embodiments, upon receiving the plurality of noise waveform signals from the sensor assembly sensors, vehicle sensors 148, and/or vehicle systems 124, the motion artifact determinant module 114 can assign a weight to each of the received noise waveform signals. The weight assigned to each of the noise waveform signals can be associated to a determined level of impact that each sensed noise waveform signal has to the motion artifacts that are contaminating the PPG measurement signal 208. The level of impact can be determined by evaluating one or more noise waveform signals that are output by one or more sensor assembly sensors, vehicle sensors 148, and/or vehicle systems 124.

Upon evaluating the one or more noise waveform signals, the motion artifact determinant module 114 can apply a respective weight to each noise waveform signal based on the type of sensors/systems that output the noise waveform signal, the location of the sensors/systems that output the noise waveform signal, the type of data that the sensors/systems that output the noise waveform signal are capturing/measuring, and the impact of the noise waveform signal on the capturing of PPG waveform signals output by one or more optical sensors 202. For example, one or more noise waveform signals that are output by biological sensors located within the one or more sensor assemblies 120 within the vehicle seat 122 can be determined to have a higher level impact and can therefore be assigned a higher weight than other noise waveform signals provided by non-biological sensors located at other areas of the vehicle 102. Upon determining the weight of each of the noise waveform signals, the motion artifact determinant module 114 can aggregate the plurality of noise waveform signals to each impact the processed motion artifacts measurement signal 210 based on an assigned weight.

In yet another embodiment, upon receiving a plurality of noise waveform signals, the motion artifact determinant module 114 can separately evaluate noise waveform signals that are attributed to movement of the driver 118 apart from noise waveform signals that are attributed to the movement of vehicle 102 itself to determine a driver motion artifacts measurement signal (not shown) and a vehicle motion artifacts measurement signal (not shown). Specifically, the motion artifact determinant module 114 can aggregate the noise waveform signals that are attributed to the movement of the driver 118 into the driver motion artifacts measurement signal. Similarly, the motion artifact determinant module 114 can aggregate the noise waveform signals that are attributed to the movement of the vehicle 102 in the vehicle motion artifacts measurement signal.

It is to be appreciated that additional methods can be utilized by the motion artifact determinant module 114 in order to process the motion artifacts measurement signal 210. In an exemplary embodiment, upon determining the motion artifacts measurement signal 210, the motion artifact determinant module 114 can send the processed motion artifacts measurement signal 210 to the PPG signal filtering module 116 in order filter the PPG measurement signal 208 and process the refined PPG signal 212.

III. Processing a Refined PPG Signal and Additional Motion Artifact Resistant Techniques The PPG signal filtering module 116 can utilize one or more techniques to decontaminate the PPG measurement signal 208 processed by the PPG determinant module 112 from motion artifacts associated with the driver 118 and the vehicle 102 itself. Processing completed by the PPG signal filtering module 116 can include amplification, mixing, and filtering of the PPG measurement signal 208 and the motion artifacts measurement signal 210, as well as other signal processing techniques known in the art, some of which are discussed below.

In an exemplary embodiment, upon receiving the motion artifacts measurement signal 210, the PPG signal filtering module 116 can apply a filter on the PPG measurement signal 208 output by the PPG determinant module 112 in order to process the refined PPG signal 212. The refined PPG signal 212 is indicative of a measurement of the driver's blood volume and blood composition that is decontaminated from the one or more motion artifacts associated with the driver 118 and the vehicle 102.

With reference to FIGS. 1 and 2B, when applying the filter, the PPG signal filtering module 116 can evaluate the motion artifacts measurement signal 210 and PPG measurement signal 208 to process the refined PPG signal 212 that is filtered from the PPG measurement signal 208. Specifically, the PPG signal filtering module 116 can determine signal segments 214 of the PPG measurement signal 208 that include data that is attributed to the PPG measurement signal 208 and data that is attributed to the motion artifacts measurement signal 210. In other words, the PPG signal filtering module 116 can determine one or more signal segments 214 of PPG measurement signal 208 that are attributed to motion artifacts associated with the driver 118 and the vehicle 102, as represented by the motion artifacts measurement signal 210.

Upon determining signal segments 214 of the PPG measurement signal 208 that includes the motion artifacts, the PPG signal filtering module 116 can filter one or more signal segments 214 of the PPG measurement signal 208 that are attributed to the motion artifacts as represented by the motion artifacts measurement signal 210 in order to extract one or more signal segments 214 that are representative of the refined PPG signal 212. Upon extraction of the one or more signal segments 214 that are representative of the refined PPG signal 212, the PPG signal filtering module 116 can process and output the refined PPG signal 212 (this process is best illustrated by the best example as presented in FIG. 2B).

In an alternate embodiment, as discussed above, the motion artifact determinant module 114 can provide separate motion artifacts measurement signals in the form of the driver motion artifacts measurement signal and the vehicle motion artifacts measurement signal that are each individually associated with the driver 118 and the vehicle 102. Upon receiving the driver motion artifacts measurement signal and the vehicle motion artifacts signal, the PPG signal filtering module 116 can apply multiple levels of filtering to the PPG measurement signal 208 in order to filter one or more signal segments 214 of the PPG measurement signal 208 that are attributed to the driver motion artifacts measurement signal separately from one or more signal segments 214 that are attributed to the vehicle motion artifacts measurement signal. It is to be appreciated that additional methods can be utilized by the PPG signal filtering module 116 in order to process the refined motion artifacts signal.

In one or more embodiments, the refined PPG signal 212 can be provided by the PPG signal filtering module 116 to the processor 106 of the computing device 104 in order to be utilized for biometric interpretation by one or more vehicle systems 124. Specifically, the computing device 104 can evaluate the refined PPG signal 212 in order to determine biometric data that is associated with the driver 118. The computing device 104 can further utilize such biometric data in order to determine one or more driver states that can be utilized to control vehicle HMI output, vehicle systems 124, and/or autonomous driving of the vehicle 102. The "driver state," as used herein, refers to a measurement of a state of the biological system of the driver. The driver state can be one or more of alert, vigilant, drowsy, inattentive, distracted, stressed, intoxicated, other generally impaired states, other emotional states and/or general health states, among others.

In alternate embodiments, alternative methods can be utilized by the system 100 in order to process the refined PPG signal 212. In one embodiment, a method of signal modulation and demodulation can be utilized in order to decontaminate the PPG measurement signal 208 from motion artifacts. More specifically, a carrier frequency can be generated at a calculated frequency of a harmonic of an identified noise component (e.g., noise waveform signal) that can be utilized to generate and demodulate an amplitude modulated signal (e.g., PPG measurement signal 208) in order to reduce signal interference. Such a method is described in Anderson et al., U.S. Pat. No. 7,623,990, filed Nov. 3, 2005, the entirety of which is hereby incorporated by reference.

In another embodiment, instead of filtering the PPG measurement signal 208 from the motion artifacts measurement signal 210 in order to process the refined PPG signal 212, the system 100 can utilize methods for minimizing the influence of motion artifacts during the measurement of PPG signals. For instance, a method of using amplitude modulated light can be used to encode the PPG signal (e.g., PPG waveform signals, PPG measurement signal 208) in order to distinguish the measured PPG signal from noise. In one embodiment, the source circuitry 204 of the optical sensor 202 can generate an amplitude modulated code sequence in the form of a Barker binary code sequence that is received by the detector circuitry 206. The Barker binary code sequence can be used to detect the segment of the signal associated to noise based on determining an activated light source and deactivated light source in order to differentiate the PPG signal from noise. Such a technique is described by R. Gircys, et. al in "Movement Artefact Resistant Photoplethysmographic Probe," Elektronika IR Elektrontechnika, ISSN 1392-1215, Vol. 20, 2014, the entire contents of which are incorporated by reference.

IV. Method for Processing PPG Signals in a Vehicle

Figure 4:
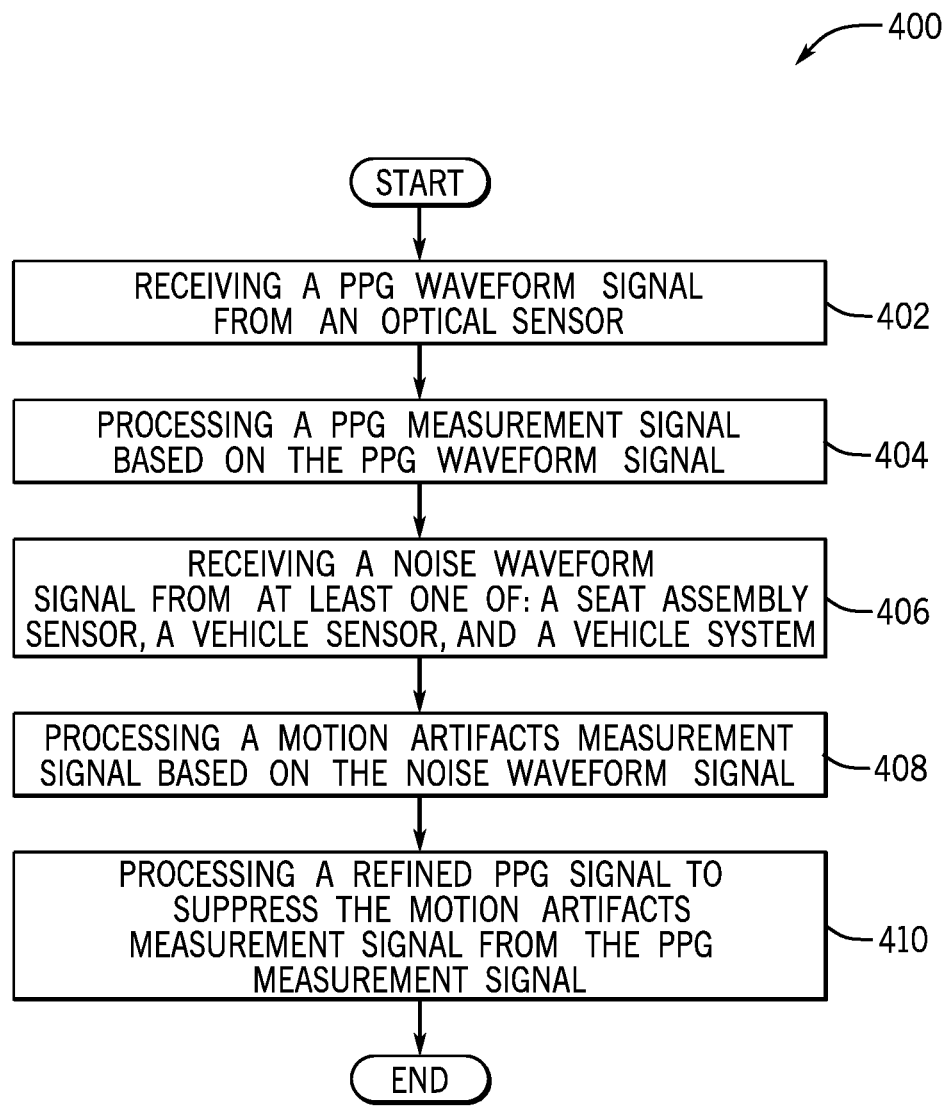
FIG. 4 is a process flow diagram of a method for processing PPG signals in a vehicle from the operating environment of FIG. 1 according to an exemplary embodiment.

Referring now to FIG. 4, a process flow diagram of an exemplary computing-implemented method 400 for processing PPG signals in the vehicle 102 is provided from the operating environment of FIG. 1 according to an exemplary embodiment. FIG. 4 will be described with reference to the components of FIG. 1, FIG. 2A, and FIG. 2B, though it is to be appreciated that the method of FIG. 4 can be used with other systems/components. At block 402, the method includes receiving a PPG waveform signal from an optical sensor. In one embodiment, as described above, one or more optical sensors 202 included within one or more sensor assemblies 120 can each output a respective PPG waveform signal to the PPG determinant module 112.

At block 404, the method includes processing a PPG measurement signal 208 based on the PPG waveform signal. In an exemplary embodiment, upon receiving one or more PPG waveform signals, the PPG determinant module 112 can convert one PPG waveform signal (e.g., the optimum PPG waveform signal) or aggregate the plurality of PPG waveform signals in order to process the PPG measurement signal 208. At block 406, the method includes receiving a noise waveform signal from at least one of: a seat assembly sensor, a vehicle sensor, and a vehicle system. As discussed in detail above, one or more seat assembly sensors, vehicle sensors 148, and/or vehicle systems 124 can output one or more noise waveform signals to the motion artifact determinant module 114.

At block 408, the method includes processing a motion artifacts measurement signal 210 based on the noise waveform signal. In an exemplary embodiment, upon receiving one or more noise waveform signals, the motion artifact determinant module 114 can convert one noise waveform signal or aggregate the plurality of noise waveform signals in order to process the motion artifacts measurement signal 210.

At block 410, the method includes processing a refined PPG signal 212 to suppress the motion artifacts measurement signal 210 from the PPG measurement signal 208. As discussed, in one embodiment, the PPG signal filtering module 116 can receive the PPG measurement signal 208 and the motion artifacts signal respectively from the PPG determinant module 112 and the motion artifact determinant module 114. The PPG signal filtering module 116 can filter the PPG measurement signal 208 by determining one or more segments of the PPG measurement signal 208 that include data that is attributed to the motion artifacts measurement signal 210. The PPG signal filtering module 116 can filter one or more signal segments 214 of the PPG measurement signal 208 that are attributed to the motion artifacts as represented by the motion artifacts measurement signal 210, in order to process the refined PPG signal 212. The refined PPG signal 212 is indicative of a measurement of the driver's blood volume and blood composition that is decontaminated from the one or more motion artifacts associated with the driver 118 and the vehicle 102.

The embodiments discussed herein may also be described and implemented in the context of non-transitory computer-readable storage medium storing computer-executable instructions. Non-transitory computer-readable storage media includes computer storage media and communication media. For example, flash memory drives, digital versatile discs (DVDs), compact discs (CDs), floppy disks, and tape cassettes. Non-transitory computer-readable storage media may include volatile and nonvolatile, removable and non-removable media implemented in any method or technology for storage of information such as computer readable instructions, data structures, modules or other data. Non-transitory computer readable storage media excludes transitory and propagated data signals.

It will be appreciated that various embodiments of the above-disclosed and other features and functions, or alternatives or varieties thereof, may be desirably combined into many other different systems or applications. Also that various presently unforeseen or unanticipated alternatives, modifications, variations, or improvements therein may be subsequently made by those skilled in the art which are also intended to be encompassed by the following claims.

The invention claimed is:

1. A computer-implemented method for processing photoplethysmography (PPG) signals in a vehicle, comprising:
receiving a plurality of PPG waveform signals output from a plurality of optical sensors included in one or more sensor assemblies;
receiving a plurality of pressure measurement signals output from a plurality of pressure sensors included in the one or more sensor assemblies;
selecting optimum PPG waveform signals from the plurality of PPG waveform signals based on the plurality of pressure measurement signals and based on a position of a driver in the vehicle;
aggregating the optimum PPG waveform signals into a PPG measurement signal;
outputting the PPG measurement signal to determine a state of the driver; and
controlling at least one vehicle system of the vehicle based on the driver state of the driver.

2. The computer-implemented method of claim 1, wherein selecting the optimum PPG waveform signals includes determining one or more of the plurality of pressure sensors sensing the highest pressure based on the plurality of pressure measurement signals.

3. The computer-implemented method of claim 2, further including selecting the optimum PPG waveform signals based on a location of the plurality of optical sensors relative to a location of the one or more of the plurality of pressure sensors sensing the highest pressure.

4. The computer-implemented method of claim 2, further including selecting the optimum PPG waveform signals output from one or more of the plurality of optical sensors included within the one or more sensor assemblies also including the one or more of the plurality of pressure sensors sensing the highest pressure.

5. The computer-implemented method of claim 1, wherein selecting the optimum PPG waveform signals based on the position of the driver further includes determining a location of a vehicle seat in the vehicle having the highest amount of contact with the driver based on the position of the driver, and selecting PPG waveform signals output from one or more of the plurality of optical sensors included within sensor assemblies located at the location of the vehicle seat.

6. The computer-implemented method of claim 1, wherein selecting the optimum PPG waveform signals based on the position of the driver further includes identifying movement of the driver and selecting PPG waveform signals output from one or more of the plurality of optical sensors included within sensor assemblies at a location in a vehicle seat proximate to a body part of the driver exhibiting the least movement.

7. The computer-implemented method of claim 1, wherein selecting the optimum PPG waveform signals based on the position of the driver further includes selecting the PPG waveform signals output from one or more of the plurality of optical sensors included within sensor assemblies located in a vehicle seat proximate to a left leg of the driver.

8. The computer-implemented method of claim 1, further including processing a refined PPG signal to suppress motion artifacts from the PPG measurement signal by filtering a segment of the PPG measurement signal that is attributed to motion artifacts represented within a motion artifacts measurement signal.

9. The computer-implemented method of claim 1, wherein selecting the optimum PPG waveform signals further includes determining the position of the driver based on images of the driver received from one or more cameras.

10. The computer-implemented method of claim 9, further including determining characteristics of clothing worn by the driver based on the images, the characteristics including at least one of color, material, clothing type, and a location of clothing on the driver.

11. The computer-implemented method of claim 10, further including controlling an intensity of optical sensors included within the plurality of optical sensors based on the characteristics of clothing and a location of the optical sensors.

12. The computer-implemented method of claim 10, further including controlling an intensity of optical sensors included within the plurality of optical sensors based on the clothing type at a location of clothing on the legs of the driver.

13. A system for processing photoplethysmography (PPG) signals in a vehicle, comprising:
a computing device that includes a memory storing instructions that are executed by a processor; and
a PPG determinant module that is included as a module of the computing device that:
receives a plurality of PPG waveform signals output from a plurality of optical sensors included in one or more sensor assemblies, receives a plurality of pressure measurement signals output from a plurality of pressure sensors included in the one or more sensor assemblies, evaluates the plurality of PPG waveform signals to determine a set of consistent PPG waveform signals including optimum PPG waveform signals selected from the plurality of PPG waveform signals based on the plurality of pressure measurement signals and based on a position of a driver in the vehicle, aggregates the set of consistent PPG waveform signals into a PPG measurement signal;

outputs the PPG measurement signal to the computing device; and controls at least one vehicle system of the vehicle based on the driver state of the driver.

14. The system of claim 13, wherein the PPG determinant module determines one or more of the plurality of pressure sensors sensing the highest pressure based on the plurality of pressure measurement signals and selects the optimum PPG waveform signals based on a location of the plurality of optical sensors relative to a location of the one or more of the plurality of pressure sensors sensing the highest pressure.

15. The system of claim 13, wherein the PPG determinant module discards PPG waveform signals from the a set of consistent PPG waveform signals based a location of the plurality of optical sensors relative to the position of the driver.

16. The system of claim 13, further including one or more cameras for capturing images of the driver, wherein the PPG determinant module determines characteristics of clothing worn by the driver based on the images, and controls an intensity of optical sensors included within the plurality of optical sensors based on the characteristics of clothing and a location of the optical sensors.

17. A non-transitory computer-readable storage medium storing instructions that when executed by a computer, which includes a processor perform a method, the method comprising:

receiving a plurality of PPG waveform signals output from a plurality of optical sensors included in one or more sensor assemblies;

receiving a plurality of pressure measurement signals output from a plurality of pressure sensors included in the one or more sensor assemblies;

selecting optimum PPG waveform signals from the plurality of PPG waveform signals based on the plurality of pressure measurement signals and based on a position of a driver in a vehicle;

aggregating the optimum PPG waveform signals into a PPG measurement signal;

outputting the PPG measurement signal to determine a state of the driver; and controlling at least one vehicle system of the vehicle based on the driver state of the driver.

18. The non-transitory computer-readable medium of claim 17, wherein selecting the optimum PPG waveform signals includes selecting PPG waveform signals output from one or more of the plurality of optical sensors that are located in proximity to one or more of the plurality of pressure sensors sensing the highest pressure.

19. The non-transitory computer-readable medium of claim 17, further including determining characteristics of clothing worn by the driver based on images received from one or more cameras, the characteristics including at least one of color, material, clothing type, and a location of clothing on the driver.

20. The non-transitory computer-readable medium of claim 19, further including controlling an intensity of optical sensors included within the plurality of optical sensors based on the characteristics of clothing and a location of the optical sensors.

* * * * *